United States Patent [19]

Srivastava et al.

[11] Patent Number: 5,670,345
[45] Date of Patent: Sep. 23, 1997

US005670345A

[54] BIOLOGICAL PRODUCTION OF HUMIC ACID AND CLEAN FUELS FROM COAL

[75] Inventors: Kailash Chandra Srivastava, Centreville; Daman S. Walia, Woodbridge, both of Va.

[73] Assignee: Arctech, Inc., Chantilly, Va.

[21] Appl. No.: 483,261

[22] Filed: Jun. 7, 1995

[51] Int. Cl.$^6$ .............. C12N 1/20; C12P 17/18; C12P 7/44; C12P 19/60

[52] U.S. Cl. .............. 435/75; 435/42; 435/119; 435/142; 435/143; 435/156; 435/167; 435/252.1; 435/281

[58] Field of Search .............. 435/252.1, 281, 435/75, 42, 142, 143, 156, 167, 101, 119

[56] References Cited

U.S. PATENT DOCUMENTS

| | | |
|---|---|---|
| 1,606,015 | 11/1926 | Blackwell . |
| 2,992,093 | 7/1961 | Burdick . |
| 3,076,291 | 2/1963 | Gardner . |
| 3,111,404 | 11/1963 | Karcher et al. . |
| 3,264,084 | 8/1966 | Karcher . |
| 3,352,902 | 11/1967 | Moschopedas . |
| 3,398,186 | 8/1968 | Schwartz . |
| 3,418,100 | 12/1968 | Cooley . |
| 3,544,295 | 12/1970 | Nakamigawa et al. . |
| 3,574,649 | 4/1971 | Fanti et al. . |
| 3,607,211 | 9/1971 | Nettesheim et al. . |
| 3,674,649 | 7/1972 | Formisano et al. . |
| 3,711,392 | 1/1973 | Metzger .............. 435/281 |
| 3,770,411 | 11/1973 | Chambers et al. . |
| 4,206,288 | 6/1980 | Detz et al. . |
| 4,274,760 | 6/1981 | Norman . |
| 4,319,041 | 3/1982 | Goff . |
| 4,321,076 | 3/1982 | Firth, Jr. . |
| 4,647,537 | 3/1987 | Shigemitsu .............. 435/178 |
| 4,659,670 | 4/1987 | Stevens, Jr. et al. . |
| 4,775,627 | 10/1988 | Attia et al. . |
| 4,882,274 | 11/1989 | Pyne, Jr. et al. . |
| 4,914,024 | 4/1990 | Strandberg et al. . |
| 4,985,060 | 1/1991 | Higa . |
| 4,997,202 | 3/1991 | Cronje et al. .............. 426/332 |
| 5,026,416 | 6/1991 | Alexander .............. 71/24 |
| 5,034,045 | 7/1991 | Alexander .............. 71/24 |
| 5,424,195 | 6/1995 | Volkwein .............. 435/42 |
| 5,486,214 | 1/1996 | Paszczynski et al. .............. 435/189 |

Primary Examiner—Herbert J. Lilling
Attorney, Agent, or Firm—Browdy and Neimark

[57] ABSTRACT

Coal is treated aerobically or anaerobically to produce humic acid, volatile fatty acids, lower alcohols, and/or methane using a consortium of bacteria designated Mic-1 or KSARC56. This process can also be used to convert aromatic compounds, such as phenols and derivatives thereof, to methane and carbon dioxide.

10 Claims, 7 Drawing Sheets

BIOLOGICAL PRODUCTION OF HUMIC ACID AND CLEAN FUELS FROM COAL

FIELD OF THE INVENTION

The present invention relates to a biological method for producing humic acid, methane, and/or volatile fatty acids from coal, as well as to consortia of microorganisms for this production.

BACKGROUND OF THE INVENTION

Coal is one of the largest fossil energy resources in the United States. This heterogeneous material consists of mainly carbon, hydrogen, and oxygen, but also contains varying concentrations of contaminants such as nitrogen, sulfur and minerals. Coals which contain significant quantities of these contaminants are called low-rank coals. Low-rank coals are undesirable for use as fuels, and government regulations prevent burning of the majority of these coals because of their high sulfur content. Moreover, the low energy content of these coals makes their use cost-prohibitive.

The use of deposits of rank coal as a feedstock for the production of clean fuels has appeal both as a use for the native fuel supply and as the precursor for an environmentally acceptable fuel. Interest in such coal conversion has been increasing in the fuel industry as a whole, and in particular in electric utilities. Although liquefaction processes can produce clean fuels from coal, these processes require extremes in pressure and temperature which render them unattractive from an economic standpoint. Biological conversion of coal via the action of microorganisms have been considered as a potential alternative for the production of fuels because of the mild and economically favorable process conditions generally associated with such conversions.

Nettesheim et al., in U.S. Pat. No. 3,607,212, disclose the use of a mixture of brown coal and a material which is capable of being decomposed by bacteria to improve soil fertility. There is no disclosure of what bacteria are used, nor of whether the coal is decomposed to produce humic acid.

Microorganisms have been used to desulfurize coal, as disclosed by Stevens et al. in U.S. Pat. No. 4,659,670; Attia et al. in U.S. Pat. No. 4,775,637; and Detz et al., in U.S. Pat. No. 4,206,288. None of these patents discloses the use of microorganisms for any function other than to reduce the sulfur content of coal.

Strandberg et al., in U.S. Pat. No. 4,914,024, disclose the use of a species of Streptomyces for solubilizing coal. An organic nitrogen source must be present in the medium which the microorganisms can modify or metabolize to exhibit coal-solubilizing activity. There is no disclosure of what the final products of the solubilized coal are, although the BACKGROUND section notes that thermal and chemical processes for conversion of coal to liquid and gaseous products have previously been used.

Pyne, Jr., et al. in U.S. Pat. No. 4,882,274, disclose a method for solubilizing low-rank coals with an enzymatic system which is free of cells. The enzyme used is obtained from a culture of white rot fungi. The biosolubilized material can be used as a feedstock for acid-catalyzed methylation to produce high quality fuels, or as a source for value-added chemicals such as surfactants or bioactive compounds.

As discussed above, it has been known to convert coal by the action of aerobic or anaerobic bacteria. Such conversion, however, while known to produce methane, carbon dioxide and organic acids, fails to provide significant, if any alcohol or humic acid production.

Currently, most alcohols are derived from food grains such as corn which are frequently unavailable and subject to cost fluctuations as the result of adverse weather conditions. In contrast, coal is readily available, and coal reserves are abundant. Needless to say, therefore, a real need exists for a viable biological process that enables the production of clean fuels such as methane and alcohols, as well as volatile fatty acids, from coal.

Soil humus, which consists of organic residues from the decomposition of plant matter, is an important soil constituent for enhancing plant growth. Formation of soil humus depends upon an adequate supply of raw organic residues and upon suitable conditions for their decomposition. Should either condition be lacking, the eventual decrease in soil humus content leads to reduced soil fertility. In this cases, it is necessary to add organic matter to increase the fertility of the soil.

Humic acid is the portion of soil humus that is soluble in alkaline solution but insoluble in acid solution. Humic acid is often added to soil to increase fertility. Humic acid is found in rotting vegetable matter and can be detected in the black slime of an ordinary compost pit in a home garden. Humic acid is also found in the brown organic matter of a variety of soils, as well as in peats, manure, lignite, leonardite and brown coal. Humic acid does not have a single unique structure, but is a mixture of intermediate chemical products resulting from the decomposition and conversion of lignin and other plant materials to hard coal. Humic acid is apparently formed by the bacterial and chemical degradation of plant tissue, but in soils it can also be formed by certain secondary process such as polymerization of polyphenols leached by rain from surface leaf litter and condensation of phenols, quinones and proteins that are provided by the action of soil microorganisms and small animals on soil carbohydrates.

Humic acid is derived from several sources, such as lignite, leonardite, peat and manure. Humic acids have a large cation exchange capacity and hold monovalent and multivalent elements very strongly. The molecular weight of humic acids ranges from about 800 to about 500,000, with the weight average molecular weight ranging from about 5000 to about 50,000. Humic acids are polyelectrolytes and are believed to form complexes with clay particles, thus enabling humic acids to bind monovalent and multivalent elements with great tenacity. When the cation exchange sites on the humic acid molecule are filled predominantly with hydrogen ions, the material is insoluble in water. However, when the predominant cations at the exchange sites are other than hydrogen, the material is called a humate.

Humic acid has been used either as a soil amendment or as a fertilizer component to increase the fertility of soils. For instance, in U.S. Pat. Nos. 3,111,404; 3,264,084; and 3,544,295, Karcher discloses a complex and expensive method for producing a dry ammonium humate fertilizer by treating a humic acid-bearing ore, such as leonardite, first with phosphoric acid then with ammonia to extract the humic acid content. Burdick, in U.S. Pat. No. 2,992,093, teaches a similar extraction process which yields dry humates which are useful as soil conditioners and fertilizers. Cooley, in U.S. Pat. No. 3,418,100, discloses particulate ammonium humate fertilizers.

Another method for extracting humic acid from a humic acid-bearing ore is disclosed by Chambers, in U.S. Pat. No. 3,770,411. In this case, a liquid humate product is obtained by reacting the ore with ammonia, then with phosphoric acid and, if desired, micronutrient elements. Schwartz et al., in U.S. Pat. No. 3,398,186, disclose using either an aqueous sulfate salt or a caustic soda solution as the extracting solution, followed by acidification to yield humic acid. Gardner, in U.S. Pat. No. 3,076,291, discloses using ammonium, potassium or sodium hydroxide to produce a humic acid-based seed germination promoter. Firth, in U.S. Pat. Nos. 4,274,760 and 4,321,076, discloses using a humate derived from rutile sand deposits to stimulate growth in foliage plants. Goff, in U.S. Pat. No. 4,319,041, discloses a method of forming a liquid humic acid product by mixing a humic acid-bearing ore, such as leonardite, with water and caustic soda.

Formisano et al., in U.S. Pat. No. 3,574,649, disclose a process for preparing humic acids and salts thereof by fermenting garbage and agricultural byproducts. This process uses garbage from which metal has been removed and relies upon microflora which are naturally present in the garbage. After this primary fermentation, the largest bodies are removed and a secondary fermentation occurs from the microflora left in the mixture. The mass left after this second fermentation is inoculated with *Gliocladium catenulatum* and further incubated, after which the mass is inoculated with *Streptomyces nigrifaciens* and further incubated. *Azotobacter chroococcum* are added to increase the humic constituents. The humic acids are extracted with diluted alkali.

Moschopedis, in U.S. Pat. No. 3,352,902, discloses that coals can be converted to humic acids by pre-oxidizing the coals and treating them with an aqueous solution of formaldehyde and alkali bisulfite, or with an aqueous solution of ammonia and formaldehyde with addition of sulfur dioxide to form a water soluble product.

Higa, in U.S. Pat. No. 4,985,060, discloses soil conditioners comprising coal ash, slag and zeolite. Microorganisms, such as a mixture of actinomycetes and photosynthetic bacteria, may be present in the soil conditioner to compete with harmful microorganisms present in the soil or using them as nutrient sources to eliminate the detrimental effects thereof, inducing propagation of useful microorganisms in the rhizosphere of the desired crop. There is no indication that the microorganisms are used to convert coal ash or slag to humic acid.

Blackwell, in U.S. Pat. No. 1,606,015, discloses a method for making humic acid containing plant foods by inoculating peat or other cellulosic material with certain soil bacteria until decomposition has occurred, then washing out the soluble products of decomposition to obtain vegetable acids to form plant foods. Lignite found in the northwestern part of the U.S. can be used after some preliminary treatment, but there is no indication of what this preliminary treatment is. The bacteria are described as being those found in fertile soil and which decompose the cellulose of vegetable matter found in the soil.

The methods for obtaining humic acid and humates disclosed in the patents cited above are generally difficult and/or impractical for use on a commercial scale.

SUMMARY OF THE INVENTION

It is an object of the present invention to overcome the above-noted deficiencies in the prior art.

It is an object of the present invention to produce humic acid from coal.

It is another object of the present invention to produce alcohols from coal.

It is another object of the present invention to produce methane from coal.

It is a further object of the present invention to produce volatile fatty acids from coal.

It is another object of the present invention to provide a consortium of microorganisms which react with coal to produce humic acid, methane, volatile fatty acids, and/or alcohols.

According to the present invention, coal is treated with a culture of microorganisms which act upon the coal to produce humic acids, methane, volatile fatty acids, and lower alcohols. One of the cultures used for this process is designated Mic-1, ATCC 55801 which was isolated from the hind guts of soil eating termites (*Zootermopsis sp*) and further improved at ARCTECH, Inc. This consortium of microorganisms was adapted via a step-wise process in which the culture was grown in increasing amounts of coal substrate. This consortium has been found to reproducibly convert coal to a mixture of humic acid, methane, volatile fatty acids, and lower alcohols.

Alternatively, coal can be converted to humic acid under aerobic conditions using a thermophilic, aerobic culture designated KSARC56. In this case the coal is cultured for about 48 hours at a temperature of up to about 60° C.

To produce humic acid, alcohols, methane and volatile fatty acids from coal, the coal is preferably slurried with water and treated with the consortium Mic-1, ATCC 55801, with gentle mixing under anaerobic conditions. The concentration of bacteria in the process ranges from about 1 to about 20% by weight of the mixture of coal, water, and bacteria. The concentration of coal in the mixture can range from about 0.01% by weight to about 50% by weight of the mixture. The process of the present invention yielded nearly a 95% conversion of coal to humic acids. Therefore, one ton of coal can produce 1982 pounds of humic acid, as well as about a 20% yield of methane, along with significant quantities of lower alcohols and volatile fatty acids.

Accumulation of metabolic by-products in the medium suppressed the metabolism of the primary coal degraders, acedogens and acetogens in the Mic-1 consortium. It was also found that the optimum pH for the methanogenic population, pH about 8.5., differs from that of other microbial populations, which generally are most active at pH about 7.5.

In order to overcome the problems with accumulation of metabolic by-products, a dual bioreactor was used. Although the process can successfully be carried out in a single bioreactor, the process is optimized in a dual bioreactor. In the dual bioreactor, acetate was allowed to accumulate in the first upflow bioreactor operating at a pH of about 7.5, and then the spent medium was transferred to a second upflow bioreactor at pH of about 8.5 where a methanogenic population finished the biomethanation reaction.

DETAILED DESCRIPTION OF THE INVENTION

Figure 7:
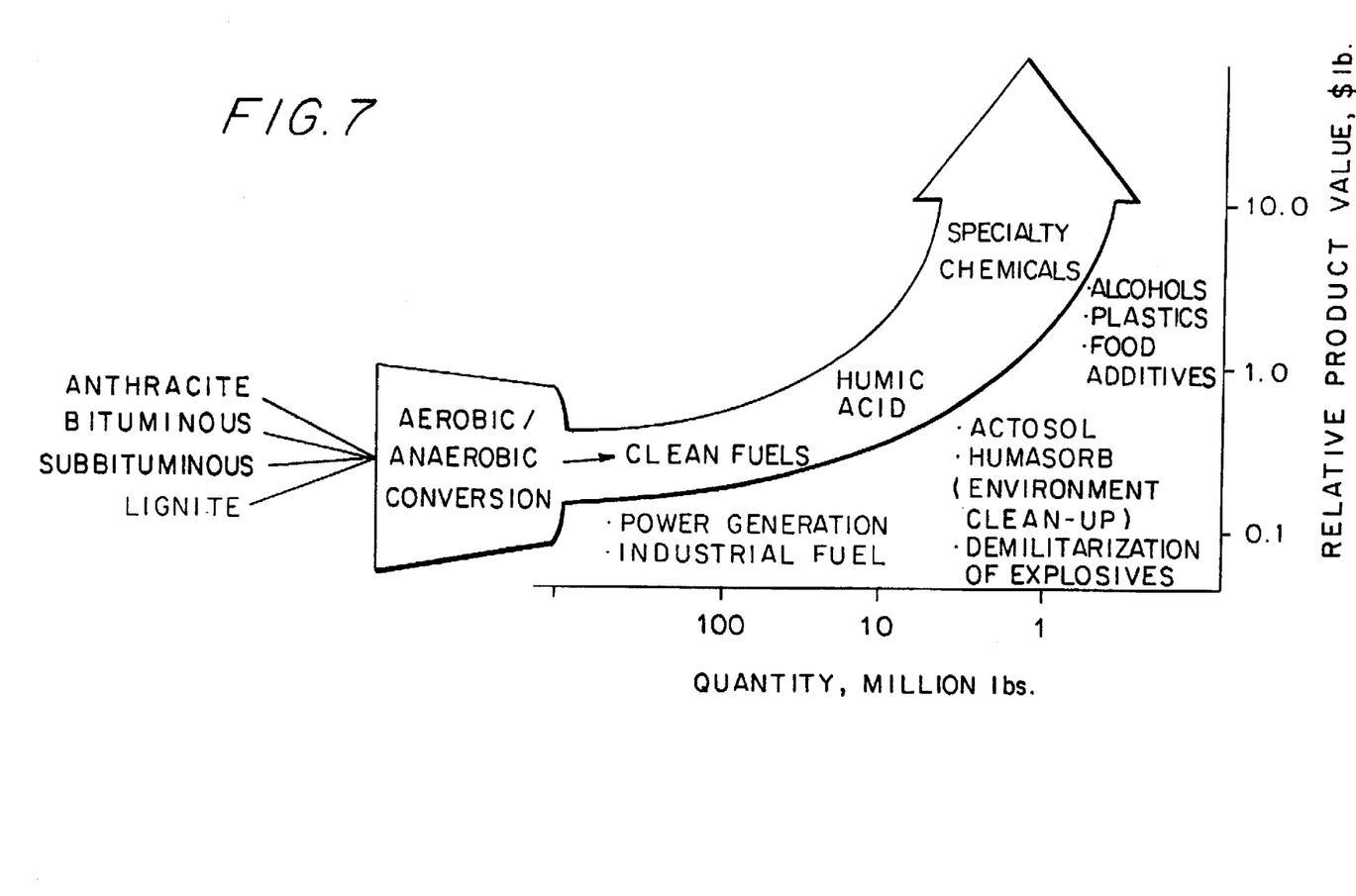
FIG. 7 illustrates the overall concept of bioconversion of coals to value added products.

FIG. 7 illustrates how bioprocessing can be used to produce high value products from coal. Low rank coals as well as anthracite, bituminous, subbituminous and lignite can be converted either aerobically or anaerobically to produce clean fuels for power generation and industrial fuel; humic acid for environmental cleanup, demilitarization of explosives, and soil treatment; and to produce specialty chemicals such as alcohols, plastics, and food additives.

The processes of coal conversion according to the present invention, using a consortium of microorganisms either aerobically or anaerobically, are economical due to near ambient treatment conditions, although optionally the treatment may be conducted at temperatures as high as 60° C. The processes are environmentally compatible, and no wastes are generated.

According to the present invention, coal is treated with a consortium of microorganisms derived from termite guts and treated, herein designated Mic-1, ATCC 55801. The coal is slurried with water and the pH is adjusted to approximately 7.8 after the coal is added to the water. The culture is maintained nearly static, although gentle mixing at 100 rpm is conveniently used to ensure contact of all of the coal with the microorganisms. The coal treatment is anaerobic, in an atmosphere of $N_2:CO_2$ of approximately 80:20. The temperature can range from about 20° C. to about 60° C., although 37° C. is a preferred temperature for ease in processing.

During coalification, the carbohydrate (cellulose) moiety of wood is aromatized, and both cellulose and lignin in wood (lignin). Furthermore, unlike lignin in the wood, even though the coal molecule contains phenolic ring structures, there are many more ether linkages, making the coal much more resistant to microbial attack than is wood. The highest ranking coal, anthracite, is the least oxidized and most highly aromatized.

A wide variety of coal can be used in the process of the present invention for preparing humic acid. These coals include anthracite, bituminous, subbituminous, mine tailings, fines, lignites and the like. Furthermore, the coal may be used either in its natural lump state or in particulate form, although pulverized coal is acted on more quickly by the microorganisms.

Figure 1:
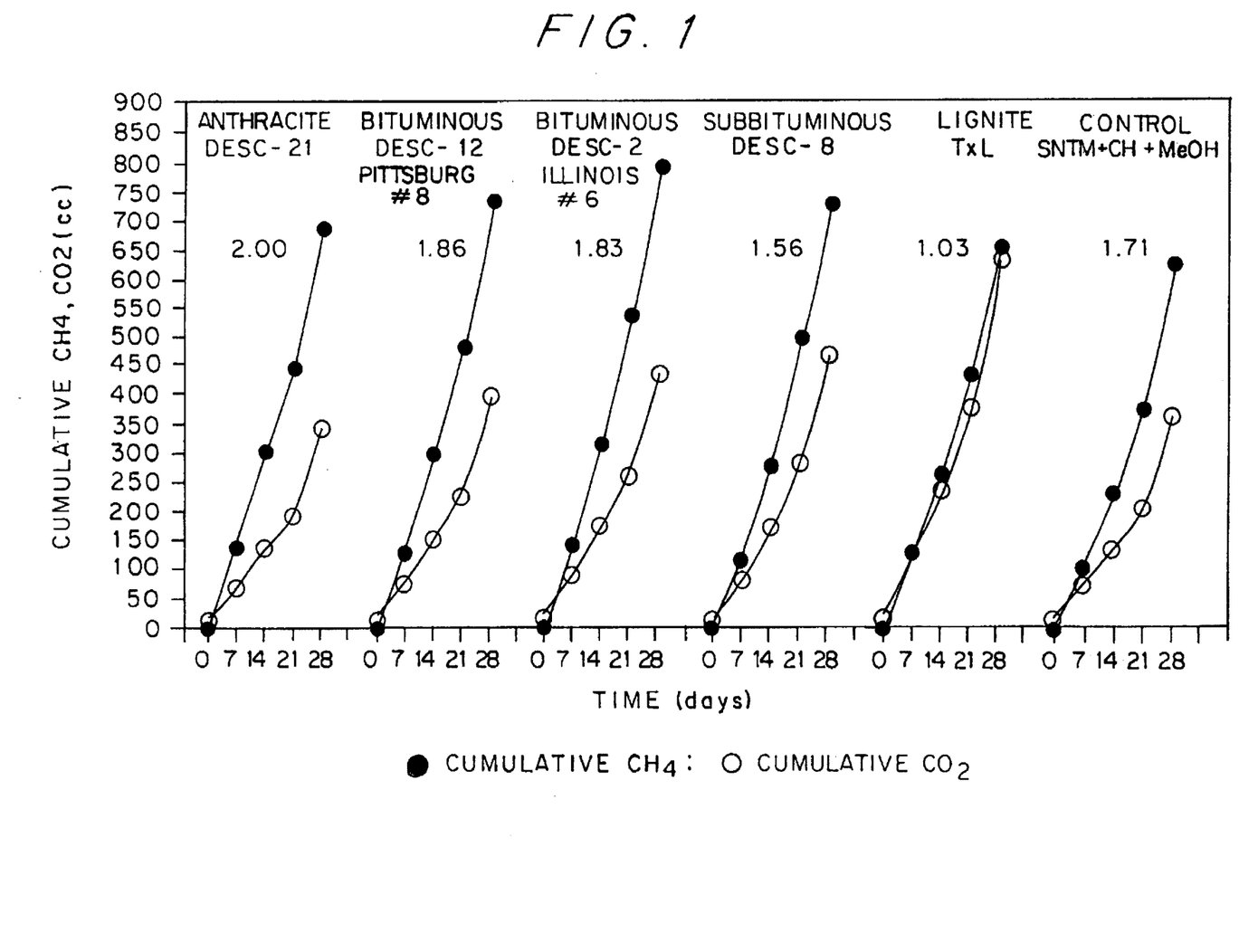
FIG. 1 demonstrates the yield of methane from treatment of coals (anthracite, bituminous, subbituminous and lignite coals) with Mic-1, ATCC 55801.
Figure 2:
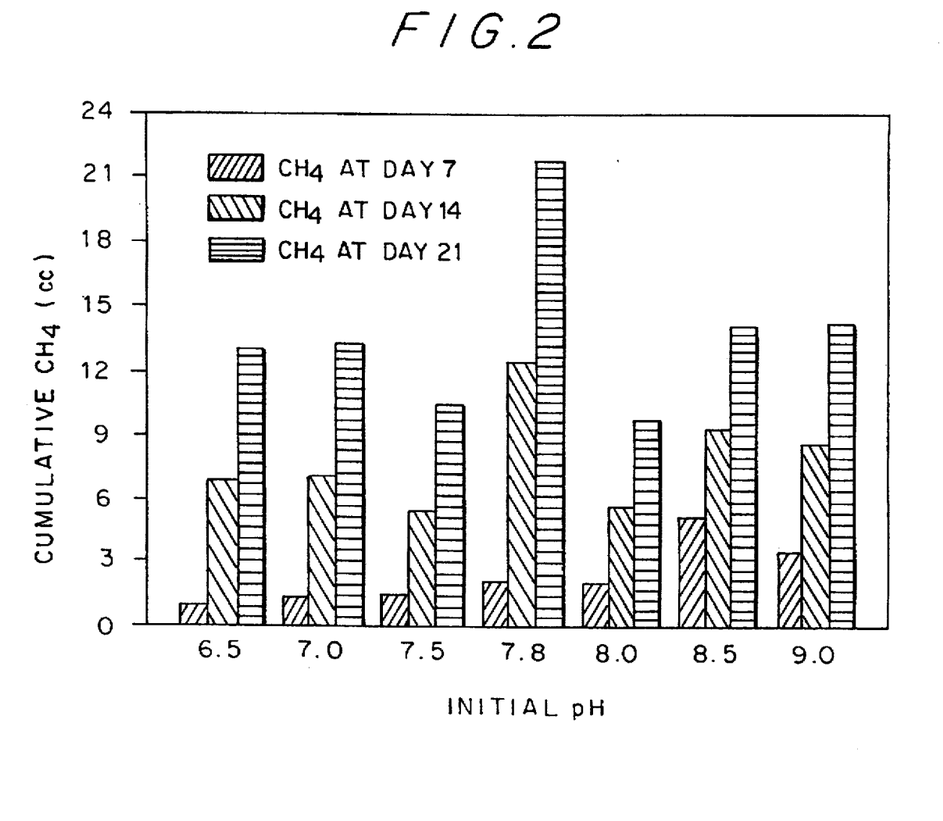
FIG. 2 shows the effect of initial pH of the medium on methane production during biomethanation of 10% Texas lignite in 0.2% medium by Mic-1, ATCC 55801 consortium.
Figure 3:
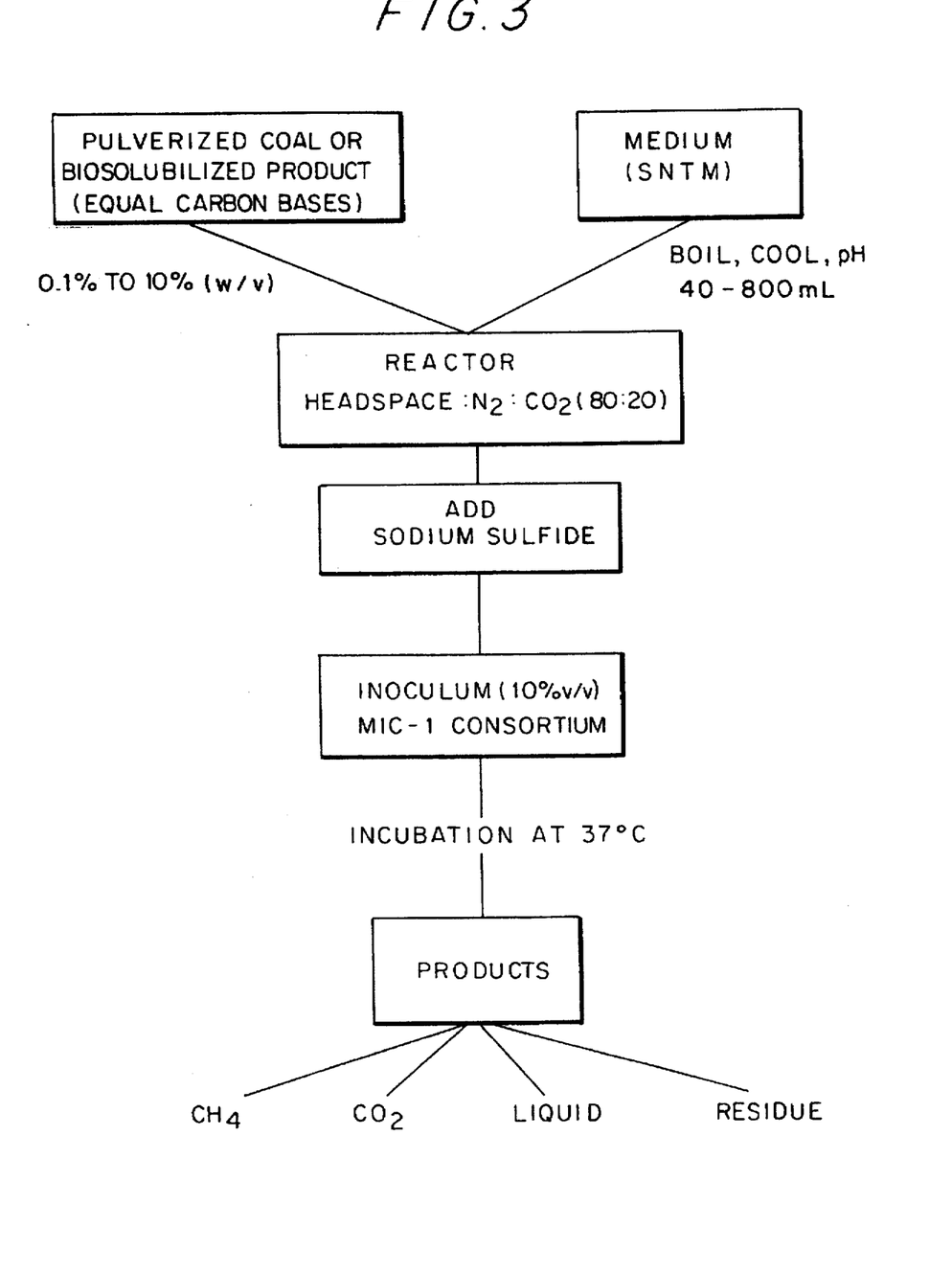
FIG. 3 shows a schematic of the process according to the present invention.

FIG. 3 shows a schematic of the process according to the present invention. Pulverized coal or biosolubilized product, e.g., round water containing aromatics such as phenols and other phenolic derivatives, at about 0.1 to 10% w/v/, is added with SNTM medium to a reactor. The reactor is maintained at anaerobic conditions, with a headspace of N2:CO2 of about 80:20. Sodium sulfide or other reducing agent which does not interfere with the bioreaction, is added and the reactor is inoculated with about 10% v/v/ of Mic-1 consortium. The reactor is incubated at approximately 37° C., and the products produced are methane, carbon dioxide, fatty acids, $C_1$–$C_4$, alcohols, including ethanol and methanol, and humic acids.

The SNTM medium, which is boiled, cooled, and the pH adjusted, is added at the rate of about 40–800 mL. The nutrients added to the reactor comprise the following:

| | |
|---|---|
| Sheftone T ™ | 2 g/L |
| Pfenning's Mineral Solution* | 10 mL/L |
| Pfenning's Trace Metals Solution* | 1.0 mL/L |
| Resazurin (0.1% solution) | 1.0 mL/L |
| KCl | 1.6 g/L |
| $NaHCO_3$ | 3.5 g/L |
| $Na_2Se_3$ (0.1% solution) | 1.0 mL/L6 |

TABLE 1

Composition of metal and mineral solutions for NTM and MSM media

| Component | Pfenning's Minerals Quantity (g/L) | Pfenning's Metals Quantity (g/L) | Mineral Solution I Quantity (g/L) | Mineral Solution II Quantity (g/L) | Mineral Solution III Quantity (g/L) |
|---|---|---|---|---|---|
| $NH_4CL$ | 8.00 | | | | |
| $CaCl_2.H_2O$ | 1.00 | 0.010 | 8.00 | | 0.02 |
| $MgCl_2.6H_2O$ | 6.60 | | 20.00 | | |
| $KH_2PO_4$ | 10.0 | | 4.0 | 4 | |
| NaCl | 8.0 | | | | |
| $H_3BO_3$ | | 0.300 | | | 0.01 |
| $CoCl_2.H_2O$ | | 0.200 | | | 0.15 |
| $FeCl_2.4H_2O$ | | 1.500 | | | |
| $MnCl_2.4H_2O$ | | 0.030 | | | 0.10 |
| $Na_2MoO_4.H_2O$ | | 0.025 | | | 0.01 |
| $NiCl_2.6H_2O$ | | 0.020 | | | 0.02 |
| $ZnSo_4.7H_2O$ | | 0.100 | | | 0.10 |
| $K_2HPO_4$ | | | | 4 | |
| $CuCl_2.H_2O$ | | | | | 0.02 |
| $FeSo4.7H_2O$ | | | | | 0.01 |
| $Na_2EDTA.2H_2O$ | | | | | 0.50 |
| $NaWO_4.2H_2O$ | | | | | 0.03 | are destroyed. As discussed above, the chemical structure of coal is much different from that of wood, the major difference being the absence of cellulose moieties in the coal. Moreover, the molecular weight of coal is much higher than any of the wood components (cellulose, hemicellulose or Methanol and a source of citrate ions, such as sodium citrate, potassium citrate, or citric acid, can also be added to the reactor to enhance the biomethanation of coal. When these compounds are added, either singly or in combination, the methanol is added at the rate of about 0.1–1.0% by weight, and the sodium citrate, potassium citrate, or citric acid is added from a 10 mM solution up to a concentration of about 1.0% by weight.

Depending upon the temperature and concentration of coal and Mic-1, ATCC 55801 in the culture, the process requires from about 21 to about 28 days to completion. The concentration of Mic-1, ATCC 55801 in the culture is generally about 10%, although concentrations of Mic-1 of from about 1 to about 20% can be used. For ease of handling and ready access to the microorganisms, the coal is pulverized.

The bioreaction with Mic-1, ATCC 55801 produces, in addition to humic acid, methane, lower alcohols ($C_1$–$C_4$ branched and straight chain alcohols) and volatile fatty acids.

EXPERIMENTAL

General Experimental Information

All manipulations were conducted under anaerobic conditions as described by Hungate and as modified by Bryant. An anaerobic glove box (Coy Corporation, Ann Arbor, Mich.) was used for culture transfer, cell washing and isolation of cell types from various microbial consortia. The anaerobic conditions in the glove box were maintained with an oxygen-free mixture of 60:40 nitrogen:hydrogen. The anaerobic conditions of the culture media, reagents, stock reservoir vessels, and bioreactors were maintained by bubbling an oxygen-free mixture of nitrogen and carbon dioxide (80:20). After preparation, the culture medium was dispensed into either pressure tubes, serum vials or Wheaton bottles. The type of vessel and working volume of medium used are summarized in Table 2. Serum vials and tubes were stoppered with butyl rubber stoppers and aluminum crimp sealed. The Wheaton bottles were stoppered with butyl rubber stoppers and screw capped.

TABLE 2

Quantity of culture medium used in different vessels

| Vessel | Total capacity (mL) | Working volume (mL) |
| --- | --- | --- |
| Pressure tube | 27 | 15 |
| 60-mL serum vial | 73 | 40 |
| 100-mL serum vial | 125 | 50 |
| 125-mL serum vial | 165 | 60 |
| 500-mL Wheaton bottle | 700 | 300 |
| 1-L Wheaton bottle | 1,250 | 500 |

For cultivation of pure cultures of methanogens, the medium was prepared in the same manner as above, but the head space of the serum vials of Wheaton bottles was exchanged with a mixture of hydrogen and carbon dioxide, 80:20.

Appropriate concentrations of Texas lignite (0.01% to 50%) were added prior to dispensing the culture medium into experimental vessels containing Texas lignite. All experiments were conducted in triplicate with the appropriate controls. Unless otherwise stated, two controls, one without nitrogen amendment, and another without Texas lignite but containing a nitrogen amendment, were a part of each experiment. All studies were conducted with −325 mesh (44μ) lignite (Texas or other) based upon the results of previous studies at ARCTECH.

The evaluation of bioconversion of lignites was based on the production of total biogas, concentration (mole %) of each of the gases (methane, carbon dioxide, nitrogen, and hydrogen sulfide) of interest, volatile fatty acids (VFA), chemical oxygen demand (COD) biomass growth, bacterial morphology, pH of the culture medium, and at the end of each experimental set, the proximate composition (ash, carbon, hydrogen, moisture, oxygen and sulfur content) of the residual Texas lignite. The data collected were analyzed to obtain kinetics for the production of methane, concentration of volatile fatty acids, soluble carbon, and biomass. These data were also used to calculate mass and electron balance according to Datta and Andrews.

Chemicals and Reagents

All chemicals used were purchased from Sigma Chemical Co., VWR Scientific Co., or Fisher Scientific Co. The nitrogen amendments (e.g., agars or peptone) used for medium preparation and microbiological procedures were purchased from Difco Laboratories, Mich. Sheftone T™ was ordered from Sheffields Products Co., NY. Cargill products were purchased from Cargill Protein Products, IO. Detailed composition of the metal, mineral and vitamin solutions are listed in Table 1. Metal and mineral solutions were dispensed in 1 L Wheaton bottles and autoclaved. B-vitamin solutions were filtered, sterilized, and stored at 4° C.

The 2.5% sodium sulfide reducing solution was prepared in an exhaust hood by first boiling one liter of double distilled water in a two liter flask. After boiling, 100 mL of the water was removed and the remaining volume (900 mL) was bubbled with nitrogen. When the water was cool, 25 g of $Na_2S.9H_2O$ was rapidly and quantitatively transferred to the 900 mL of water using the 100 mL that had previously been removed. When the $Na_2S$ was completely dissolved, the final volume was adjusted to one liter, and 7–8 mL of concentrated hydrochloric acid was added to adjust the pH to 9. The sodium sulfide solution was dispensed in 80 mL aliquots in 125-mL serum vials, and nitrogen was bubbled through the vials for 5–8 minutes. The vials were then stoppered, crimp sealed and autoclaved at 121° C. for twenty minutes.

Culture Media

Several culture media were used for the maintenance of anaerobic cultures and bioconversion of low rank coals. Yeast extract+tryptic soy broth (YE/TSB) solution, other nitrogen amendments, chelators, vitamins or substrates other than coal, were always added as concentrated solutions under aseptic and anaerobic conditions. The medium was always prepared in such a manner that the medium components were not diluted by the additions. Mic cultures were grown in various media as described in Table 3. The Sheftone New Termite Medium (SNTM) and Sheftone New Termite Medium with citrate and methanol (SNTM-CM) are simply a variant of the NTM medium. Methanogens-Sludge Medium (MSM) was used for maintenance of the methanogens, and unless otherwise indicated, the MSM was autoclave sterilized at 121° C. at 15 psi. Anaerobic conditions of all media was ensured by adding 2.5% sodium sulfide (1 mL/20 mL medium) and 0.1% resauzurin. Detailed media composition is listed in Table 1.

TABLE 3

Culture Media used for maintenance Mic anaerobic cultures

| Medium | Organic N Source | B-Vitamin Solution | Additional Changes |
|---|---|---|---|
| NTM[a] | YE/TSB[d] | + | N/A[e] |
| SNTM[b] | Sheftone T ™ (0.01 to 0.2%) | − | N/A |
| SNTM-CM[c] | Sheftone T ™ (0.01 to 0.2%) | − | Sodium Citrate and Methanol |

[a]New Termite Medium
[b]Sheftone New Termite Medium
[c]Sheftone New Termite Medium + 10 mM Sodium Citrate and 0.5 MeOH (v/v)
[d]Yeast Extract + Tryptic Soy Broth
[e]Not Applicable

Microbial Cultures

Four anaerobic, microbial consortia were used for biogasification of low rank coals. The anaerobic consortia were derived from the hind gut of wood-eating termites fed on coal. Mic-1, ATCC 55801, was derived from *Zootermopsis sp.* and Mic-4 from *Nasutitermes sp.* Mic-2 was developed at ARCTECH during studies performed in a rotating biological contactor. Mic-3 was also developed at ARCTECH by mixing consortia from different sources. The stock cultures were maintained frozen in 5.0% glycerol vials at −70° C. The working cultures were prepared by thawing the frozen stock cultures at room temperature and subsequent transfers under aseptic and anaerobic conditions into serum vials or Wheaton bottles containing medium and 0.1 to 1% Texas lignite, −325 mesh. All working stock cultures were incubated at 37° C. under stationary conditions for 14 to 21 days. Then, 500 mL Wheaton bottles containing 300–400 mL NTM+0.1% Texas lignite were inoculated with the microbial consortia to be tested. Alternatively, in order to check the stability of the consortia and avoid erroneous results due to residual Texas lignite from inocula, inoculum was prepared in bottles containing NTM without Texas lignite. After appropriate incubation time, 10 to 21 days, the cultures were aseptically harvested under anaerobic conditions, washed twice with the NTM (without YE/TSB), and resuspended in a quantity of NTM (without YE/TSB) that would give sufficient inoculum to perform the experiment. This method of inoculum preparation also provided a means for keeping the initial bacterial inoculum size constant for different treatments within a given experiment. The bacterial numbers were spectrophotometrically quantified by measuring the absorbance of the resuspended bacterial suspension at 660 nm.

Four methanogenic cultures, *Methanobacterium formicicum*, *Methanospirillum hungatii*, *Methanosarcina sp.* and *Methanothrix sp.*, were obtained from other researchers and from the University of Oregon Microbial Culture Collection. These cultures were grown and used for the acetate, formate and $H_2$—$CO_2$ conversion studies, since these methanogenic cultures are known to be present in the consortia.

Isolation of Bacterial Cultures

The consortia were diluted to $10^{-3}$ to $10^{-4}$ in sterile, buffered water. Spread plates with 15 mL NTM+2% w/v agar were prepared, and 0.1 mL of the dilution was spread onto the solidified medium surface. The final dilution factor of the cultures was $10^{-4}$ and $10^{-5}$, respectively. A 5 mL NTM+2% agar overlay with either −325 mesh Texas lignite (0.5% w/v) or biosolubilized Texas lignite (1.25% w/v) was melted, well mixed, and poured onto the inoculated NTM Petri plates. Control plates were prepared using overlays without coal supplements. The melted overlay was held at 45° C. until use; this is the temperature at which agar remains molten, but this temperature does not adversely affect the bacteria of the consortia for the short time they are exposed to this temperature.

Because it was believed that plating the cultures on the medium surface did not allow adequate contact between the bacterial cells and the coal particles, the dilution was then added directly to the coal overlay before pouring it onto the Petri dish.

Microbial Growth and Biomass Production

All of the microbial cultures/consortia were routinely observed by epifluorescence microscopy using a phase-contrast microscope (Olympus, Model BH 2) equipped with a camera. However, total microscopic cell counts and turbidimetric measurements were not a reliable quantitative method due to adherence of microbial cells to coal particles and the physical interference of coal particles with turbidimetric measurements. Instead, microbial growth was measured as total cellular protein.

The protein analysis method (Pierce, Protein Assay #23225) was developed at ARCTECH by modifying the BCA™ to monitor the changes in microbial growth A 1 mL aliquot of the culture medium was withdrawn and either analyzed the same day or preserved by freezing the sample with 80 μL of DMSO. The soluble protein in the medium was removed by centrifugation at 12,000 rpm to 10 minutes. The pellet containing either the cells (control) or cells+coal (experimental) was washed with physiological saline. The sample was centrifuged again to pelletize the cells and coal particles. Cellular protein was then solubilized by adding 1% w/v sodium dodecyl sulfate (SDS). The sample was centrifuged again at 12,000 rpm for ten minutes. Solubilized protein in the supernatant was determined using the BCA™ Protein Assay.

The assay protocol, which has linearity in the range of 5–250 μg/mL of protein required incubation of the reaction mixture of 30 minutes at 60° C. The change in color was recorded as absorbance at 562 nm against an appropriate blank and compared to a standard curve (bovine serum albumin 2.0 mg/mL in a 0.9% aqueous NaCl solution) at various concentrations to determine the protein concentration.

Biomass was also measured as wet cell weight, spectrophotometrically at 660 nm ($OD_{660}$), and dry cell weight. The dry cell weight was determined as follows: A 10 mL sample from each of the cultures was dispensed into a tared, dry, aluminum weight pan. to correct for the contribution of medium components, another aliquot was centrifuged at 10,000 rpm for 30 minutes to remove bacterial cells. A 10 mL sample of the cell-free supernatant was dispensed into another tared, dry aluminum weight pan. Both samples were dried to constant weight at 110° C. The dry cell weight was calculated by deducting the weight of the centrifuged sample from the weight of the sample which was not centrifuged. From these date, the specific growth rate (μ) was calculated.

During the exponential phase, the specific growth rate, μ, of a culture can be described as:

$$\mu = (lnx_2 - lnx_1)/t_2 - t_1$$

where $x_1$ is the biomass at time $t_1$ and $x_2$ is the biomass at time $t_2$. Both $x_2$ and $x_1$ were measured during the exponential phase. The biomass doubling time, $t_d$, was determined with the following equation:

$$t_d = (\ln 2)/\mu$$

Determination of Headspace Gas

Gas samples from the tubes, serum vials, and Wheaton bottles were measured by a syringe for either type of reactor. Total volume of biogas from the bench-scale reactors was measured by water displacement. Samples for headspace gas analyzers were obtained by directly introducing the needle of a pressure tight gas syringe into the butyl rubber stoppers on the sample containers. Prior to sample, in the pressure tight syringe was made anaerobic by flushing it with oxygen-free nitrogen and carbon dioxide mixture at least three times.

Headspace gas composition was determined using gas chromatography. A GOW-MAC (Model 580) gas chromatograph fitted with a 10'×⅛" stainless steel column packed with 100/120 mesh Carboseive S-II (Supelco Co.) was used to analyze the gas samples The conditions were: thermal conductivity detector (TCD), column temperature 200° C., detector and injector temperatures 220° C., detector current 1770 mA. Helium was used as a carrier gas (34 mL/min at 50 psi on the cylinder). The data were integrated by an HP integrator (Model 3396A). The calibration standard was prepared with a mixture of carbon dioxide, 29/3%; carbon monoxide, 10.5%; hydrogen, 4.9%; nitrogen, 24.9%; and methane, 30.7%.

Hydrogen sulfide concentration was monitored using another gas chromatograph, Varian Model 3700, equipped with flame photometric detector.

Kinetics of Methane Production

These experiments were performed to evaluate initial biomethanation of Texas lignite by the Mic-1, ATCC 55801 consortium. The experiments were performed in 60-mL serum vials or Wheaton bottles containing NTM and 0.01% Texas lignite. Methane production as a function of time was evaluated.

Effect of Agitation

Mic-1, ATCC 55801, consortium was grown in vials containing NTM+0.01, 1.0, 5.0 and 10% Texas lignite. These cultures were cultivated with and without agitation (gentle mixing at 100 rpm), and each sample was monitored for methane production and chemical oxygen demand. Each sample was also examined microscopically to monitor the bacterial cell populations attached to the coal particles.

Determination of Chemical Oxygen Demand

Total soluble carbon was colorimetrically measured as chemical oxygen demand by a method available commercially from Hach Company. For this study, a 1 mL aliquot was centrifuged at 7000 rpm for 10 minutes to remove the suspended solids. An aliquot of 500 μL was added to the reaction mixture along with 1.5 mL of deionized water, incubated at 150° C. for two hours, and the absorbance measured spectrophotometrically on a Spectronic 21 at 620 nm.

Analysis of Volatile Fatty Acids

Volatile fatty acids were analyzed using capillary gas chromatography (Hewlett Packard 5880 A) fitted with an automatic sampler according to the ASTM procedure E-260. A bonded phase, wide bore, Nukol fused silica capillary column, 15 m×0.53 mm ID, 0.5 μm film thickness (Supelco #2-5326) was used. The flame ionization detector was operated at 300° C. A thermal gradient program with initial oven temperature of 48° C. and final temperature of 200° C. was used. The initial rate was 15° C./min up to 120° C. followed by 10° C./min up to 155° C. and then 5° C./min to 200° C. held for 20 minutes. The injector temperature was 205° C. Data were integrated by an HP electronic integrator. Helium was used as the carrier gas at 5 mL/min (110 psi at the pressure regulator on the cylinder). The calibration standard for volatile fatty acids was a mixture of acetic, n-butyric, iso-butyric, propionic, valeric, iso-valeric, caproic, iso-caproic, and heptanoic acids, mixed with acetone, n-butanol, methanol, ethanol, and propanol. Prior to analysis, the stock solutions and samples were acidified with 50 mM phosphoric acid.

Dual UFBR

Figure 4:
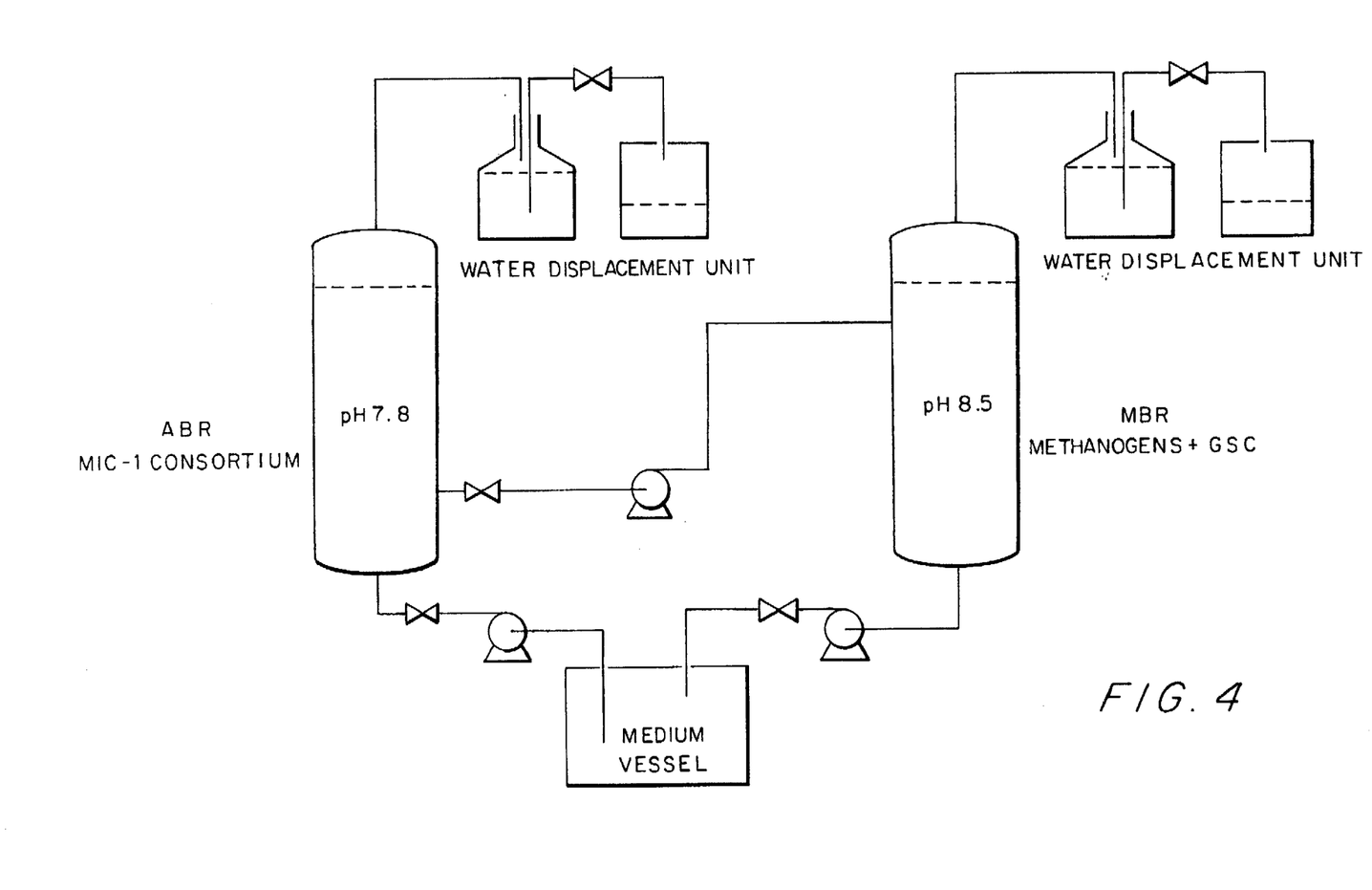
FIG. 4 shows an experimental setup for biomethanation of Texas Lignite by Mic-1, ATCC 55801 Consortium in a dual reactor.
Figure 5:
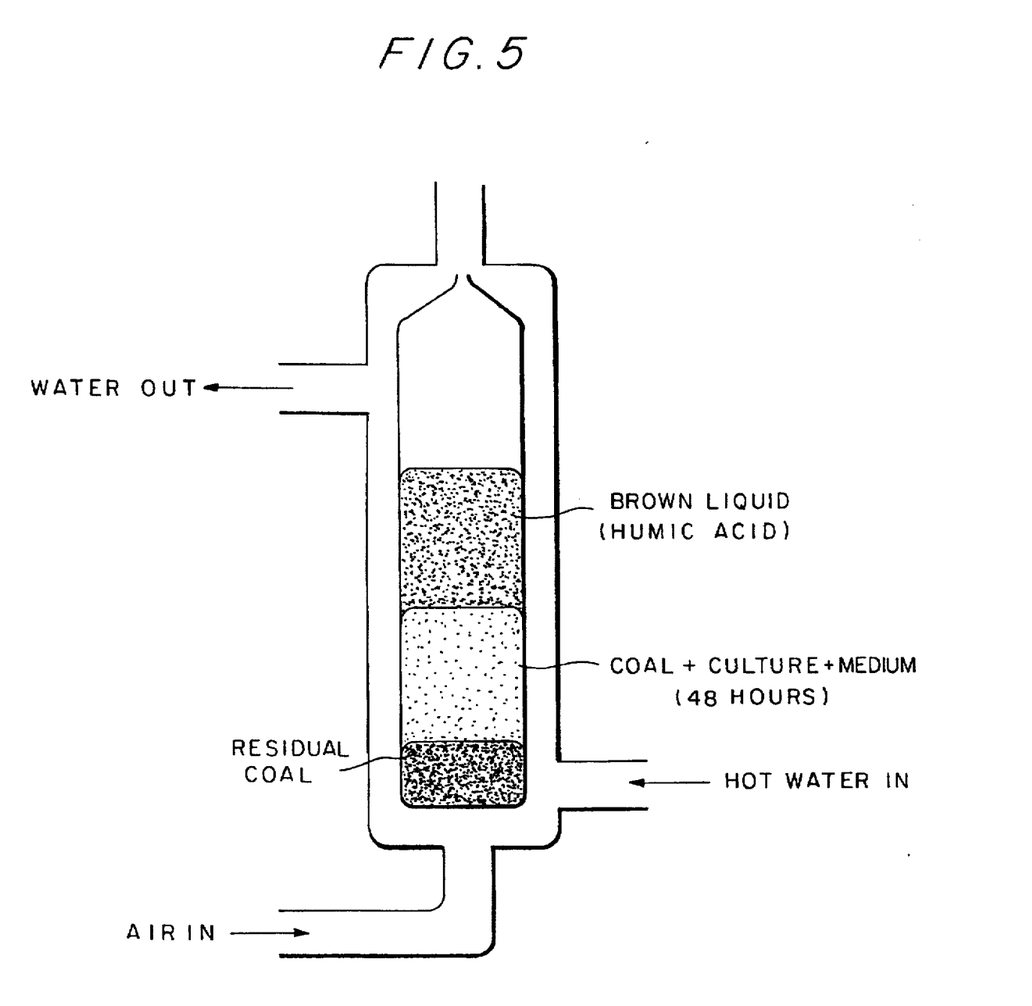
FIG. 5 shows conversion of coal by a thermophilic, aerobic culture, KSARC56.
Figure 6:
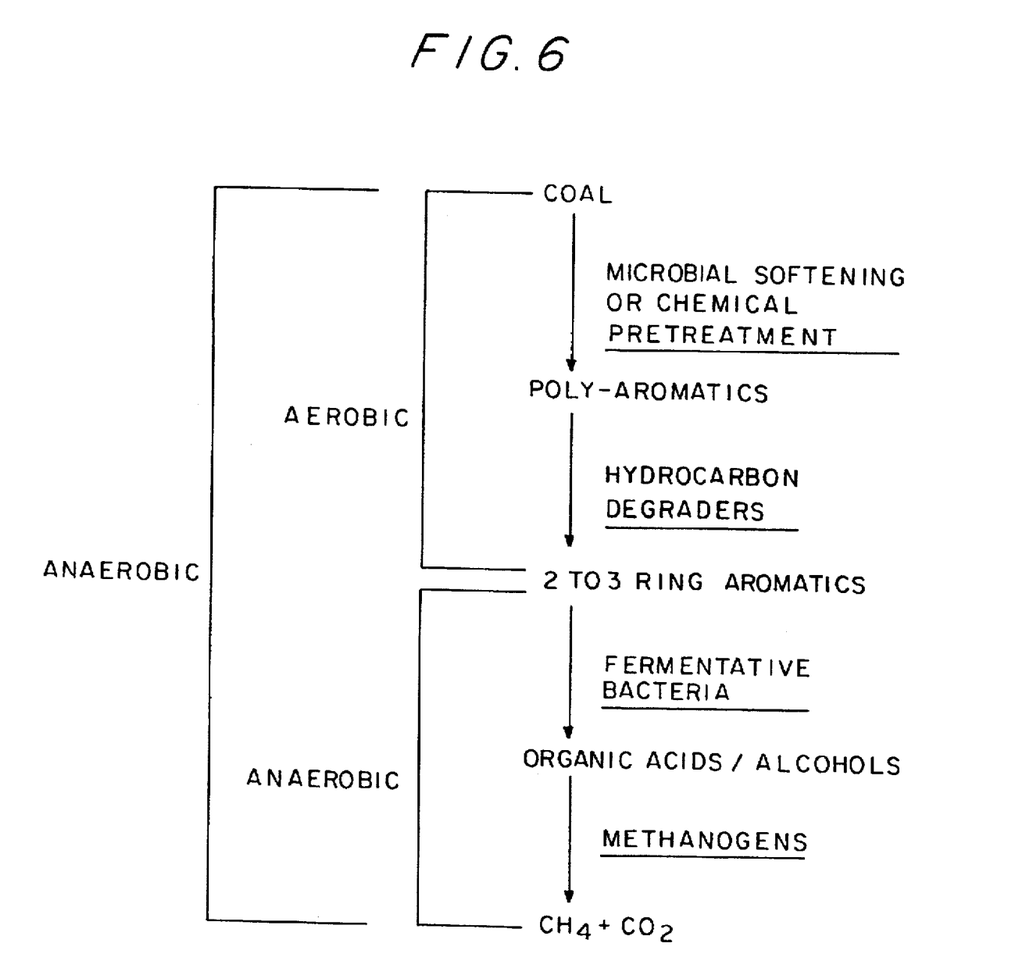
FIG. 6 illustrates concepts for bioconversion of coal.

The dual UFBR, shown in FIG. 4, is a set of interconnected "acetogenic" (ABR) and "methanogenic" (MBR) bioreactors. The ABR contained fermentation medium and anaerobic microorganisms, which are the primary coal degraders, acedogens and acetogens (Mic-1). The MBR contained methanogens and granulated sludge consortium, specially adapted for coal bioconversion. Acedo- and acetogens in Mic-1, ATCC 55801, consortium biodegrade Texas lignite and lower volatile fatty acids, such as propionate, isobutyrate, etc. However, accumulation of acetate in the medium can suppress the metabolism of acedo- and acetogens. Methanogens, on the other hand, convert acetate to methane, which allows acetogens to further convert lower volatile fatty acids to acetate. The acetate in MBRs will be consumed by methanogens for their growth and metabolism. Therefore, the hypothesis to be tested was: Texas lignite in the ABRs will be bioconverted into low-molecular volatile fatty acids by the Mic-1, ATCC 55801 consortium. At the same time, methanogens+granulated sludge consortium will grow and produce metabolites and some methane in MBRs. After a definite period of item, the essential nutrients for Mic-1 consortium, ATCC 55801 will decrease in ABR, while the concentration of acetic acid, the main substrate for methanogens, will increase. This arrangement provides better process control because of the different pH optima ranges of the two organisms.

Bacterial Morphology

Commonly observed morphologies constituting the Mic-1 consortium, ATCC 55801, shown in Table 4, were single cells, chains, or clumps of cocci, rods (predominantly short, <3 μm) of various lengths and thickness, curved and straight rods, both motile and non-motile rods, spore forming rods and coccobacilli. Four morphologies of methanogens were evident: *Methanococcus sp.*, *Methanothrix sp.*, *Methanosarcina sp.*, and short rods. The short rods appeared after two weeks of incubation. As expected, the overall numbers of methanogens increased with time. Notable changes occurring in the consortium as a function of time were an increase followed by a decrease in the number of short rods, appearance of coccobacilli (possibly *Methanosarcina sp.*) and the appearance of short curved rods.

TABLE 4

Bacterial Morphology of Mic-1 Consortium ATCC 55801

| Predominant Morphologies | Methanogens | Major Cultural Changes |
| --- | --- | --- |
| Cocci short rods (<3 μm), long rods, and long filaments | Methanococcus sp., Methanosarcina sp., Methanothrix sp., short rods | Increase in "coccobacilli". After 2 weeks: appearance of short curved rods, increase followed by decrease in the number of short rods, increase in number of methanogens |

Conversion of Coal to Humic Acids

Table 5 shows the conversion of different types of coal to humic acids, based upon a 10% solids loading of biologically treated coal.

TABLE 5

| Coal | % Coal biologically converted to humic acid |
| --- | --- |
| Anthracite | 51.1 |
| Bituminous- Pittsburgh #8 | 50.0 |
| Bituminous- Illinois #6 | 43.2 |
| Subbituminous | 81.5 |
| Texas Lignite | 86.8 |

Of the volatile fatty acids produced by the process of the present invention, acetic acid, butyric acid, and propionic acid are produced in the greatest quantities. Of the $C_1$–$C_4$ alcohols produced by the process of the present invention, ethanol is produced in the greatest quantity.

Conversion of Coal to Volatile Fatty Acids and Alcohol

Table 6 illustrates the concentration of volatile fatty acids and ethanol obtained from culturing individual bacterial isolates from either Mic-1, ATCC 55801 or Mic-4 on 0.1% Texas Lignite.

TABLE 6

Concentration of Volatile Fatty Acids and Ethanol in the Culture Broth of Individual Bacterial Isolates from Mic-1 and Mic-4 Consortia Grown on 0.1% Texas Lignite.

| | Concentration (ppm) After 14 Days of Incubation | | | | |
| --- | --- | --- | --- | --- | --- |
| Isolate[a] | Acetic Acid | Butyric Acid | Propionic Acid | Ethanol | Other VFAs |
| M1-1 | 268 | 78 | 99 | ND[b] | 204 |
| M1-2 | 298 | ND | 32 | ND | 149 |
| M1-3 | 291 | 73 | 96 | ND | 211 |
| M1-4 | 166 | 88 | ND | 29 | 179 |
| M1-5 | 293 | 76 | 92 | ND | 213 |
| M4-1 | 404 | ND | 55 | ND | 195 |
| M4-2 | 58 | 22 | ND | 27 | ND |
| M4-3 | 258 | ND | 120 | ND | 197 |
| M4-4 | 176 | 84 | ND | 46 | 152 |
| M4-5 | 357 | ND | 38 | ND | 173 |
| M4-6 | 272 | 87 | 93 | ND | 215 |
| M4-7 | 129 | 104 | 36 | ND | ND |
| M4-8 | 64 | 24 | ND | 31 | ND |

[a]Isolates derived from Mic-1 ATCC 55801 are designated as M1; those derived from Mic-4 are designated as M4.
[b]ND = non-detectable levels It can be seen from Table 6 that the isolates from consortia according to the present invention produce significant quantities of many useful products from coal. Of particular importance is M1-4, derived from Mic-1, ATCC 55801, which when grown in 0.1% Texas Lignite produced 29 ppm of ethanol after 14 days of incubation.

To favor alcohol formation, a consortium of Mic-1 was mixed with coal to form an aqueous stock broth. This aqueous stock broth was maintained under biological metabolizing conditions for a growth period of from five to five hundred days. After this period a small portion of bacteria were removed from the aqueous stock broth and mixed with carbonaceous fossil fuel to form an aqueous enrichment broth. This latter step was repeated from five to five thousand times. The bacteria obtained from this aqueous enrichment broth were mixed with carbonaceous fuel to provide an aqueous production broth. Carbonaceous fuel was continuously added to the aqueous production broth while an alcoholic solution was continuously removed from the aqueous production broth. The lower alcohols were then recovered from this solution by conventional recovery means.

The foregoing description of the specific embodiments will so fully reveal the general nature of the invention that others can, by applying current knowledge, readily modify and/or adapt for various application such specific embodiments with out departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

What is claimed is:

1. A method for producing humic acid from coal comprising introducing coal into a medium containing an anaerobic culture Mic-1, ATCC 55801, for a minimum period of time to convert said coal to humic acid.

2. A method according to claim 1 wherein said medium contains a bioenhancer for said method, said bioenhancer selected from the group consisting of methanol, citric acid, potassium citrate, sodium citrate, and mixtures thereof.

3. A method according to claim 1 wherein said culture Mic-1, ATCC 55801, is present in the amount of from about 1 to about 20% by weight of the coal.

4. The method according to claim 1 wherein the coal is selected from the group consisting of anthracite, bituminous, subbituminous, and lignites.

5. The method according to claim 1 wherein the coal is obtained from mine tailings.

6. The method according to claim 1 wherein the coal is slurried with water and the pH is adjusted to approximately 7.8.

7. The method according to claim 1 wherein the method is conducted at a temperature of up to about 60° C.

8. The method according to claim 1 wherein the method is conducted in an atmosphere of $N_2:CO_2$ of about 80:20.

9. A method for producing humic acid, methane gas, and volatile fatty acids from coal comprising introducing coal into a medium containing an anaerobic culture Mic-1 for a minimum period of time to convert said coal to humic acid, methane gas, volatile fatty acids, and lower alcohols.

10. A method for producing methane gas from coal comprising introducing coal into a medium containing an anaerobic culture Mic-1 for a minimum period of time to convert said coal to methane gas.

* * * * *